Figure 1:
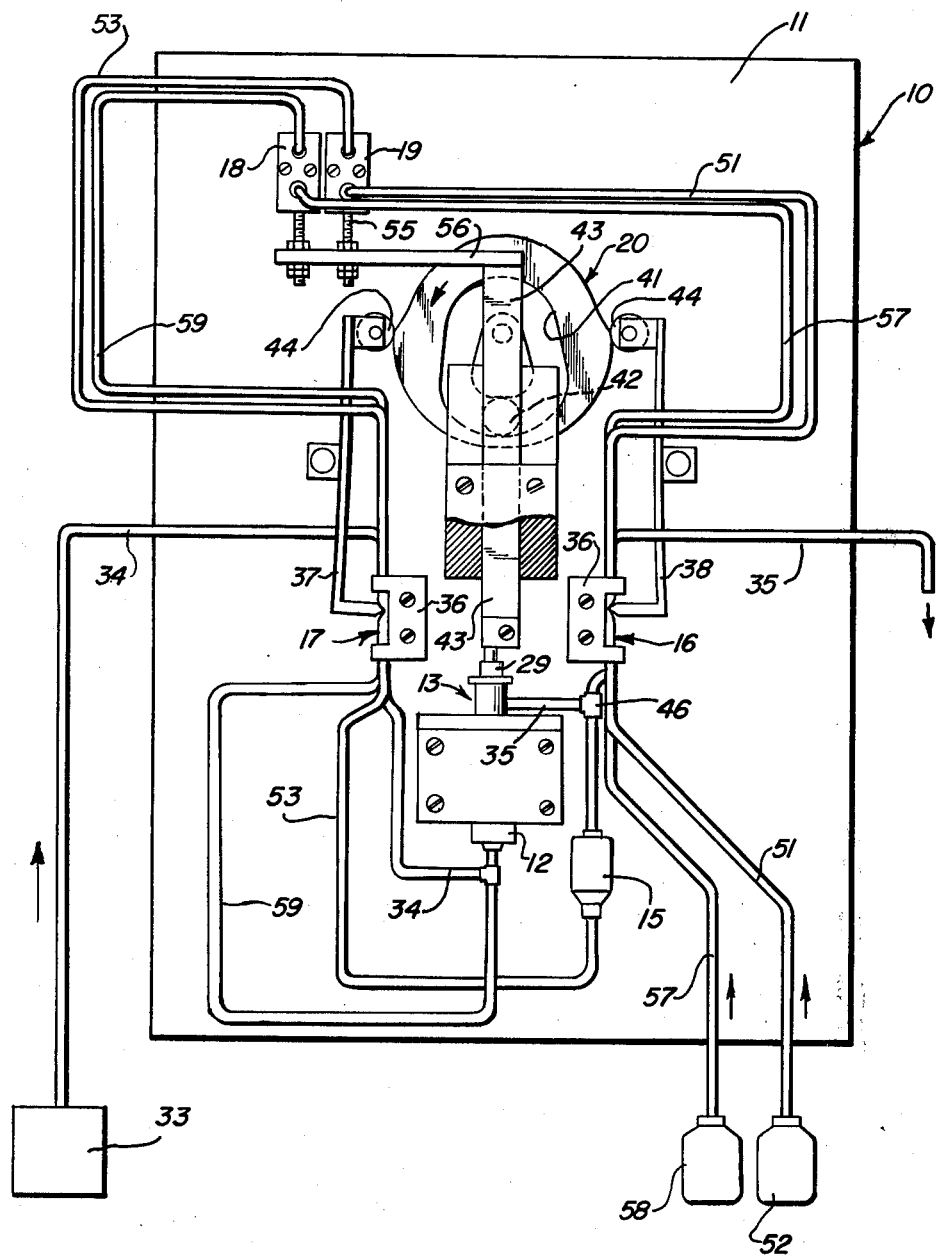

United States Patent [19]

Hach

[11] 4,288,308
[45] Sep. 8, 1981

[54] CONTINUOUS PH METER

[75] Inventor: Clifford C. Hach, Loveland, Colo.

[73] Assignee: Hach Chemical Company, Loveland, Colo.

[21] Appl. No.: 156,936

[22] Filed: Jun. 6, 1980

[51] Int. Cl.³ .......................................... G01N 27/38
[52] U.S. Cl. ........................... 204/195 R; 204/195 G; 324/438
[58] Field of Search ................... 324/438; 204/195 G, 204/195 R, 1 H

[56] References Cited

U.S. PATENT DOCUMENTS

| | | | |
|---|---|---|---|
| 2,311,976 | 2/1943 | Coleman | 324/438 |
| 2,383,450 | 8/1945 | Coleman | 324/438 |
| 3,953,136 | 4/1976 | Hach | 356/181 |
| 4,021,199 | 5/1977 | Mukae et al. | 204/195 R X |

*Primary Examiner*—G. L. Kaplan
*Attorney, Agent, or Firm*—Leydig, Voit, Osann, Mayer & Holt, Ltd.

[57] ABSTRACT

A glass pH measuring electrode is mounted in a piston that reciprocates in a chamber which is in fluid communication with a reference electrode. Intake and outlet lines to the chamber are controlled by valves. A drive means operates the piston and the valves to pull successive liquid samples into the chamber for measurement and then to discharge them. The drive means also controls two positive displacement pumps, one of which feeds controlled amounts of electrolyte past the reference electrode and the other feeds a bacterial sterilizing agent to the chamber. The electrolyte flow past the reference electrode and into the discharge flow from the chamber maintains open electrical communication with the chamber. A deformable body, preferably a bed of finely ground methyl methacrylate grit, in the chamber engages and cleans the glass electrode as the piston reciprocates.

6 Claims, 2 Drawing Figures

CONTINUOUS PH METER

This invention relates generally to chemical testing apparatus and more particularly concerns a meter for continuously monitoring the pH of a liquid sample.

pH is a measurement of the acidity or alkalinity of a solution, and it is well known to measure pH by immersing a glass measuring electrode and a reference electrode in the solution and noting the difference in electrical potential sensed, which is directly proportional to the solution pH. Typically, the reference electrode electrically contacts the solution being tested via electrolyte at what is termed a junction.

A pH meter for continuous long-term monitoring must in some way retain the critical operating properties of a clean glass surface on the measuring electrode and a flowing, uncontaminated junction for the reference electrode. If bacteria is present in the liquid being tested, as would be the case in sewage plant control or river water monitoring, bacterial growth can also interfere with long-term operation of a pH meter.

It is the primary aim of the invention to provide a simple, relatively inexpensive pH meter intended for long term, continuous and accurate pH metering.

More specifically, it is an object of the invention to provide a pH meter as characterized above having a controlled, positive flow of reference electrode electrolyte to keep the junction uncontaminated, and also having a positive mechanical cleaning action for the glass measuring electrode.

Another object is to provide a meter of the above kind which readily permits sterilizing the liquid samples under test so as to obviate bacteria problems.

Figure 2:
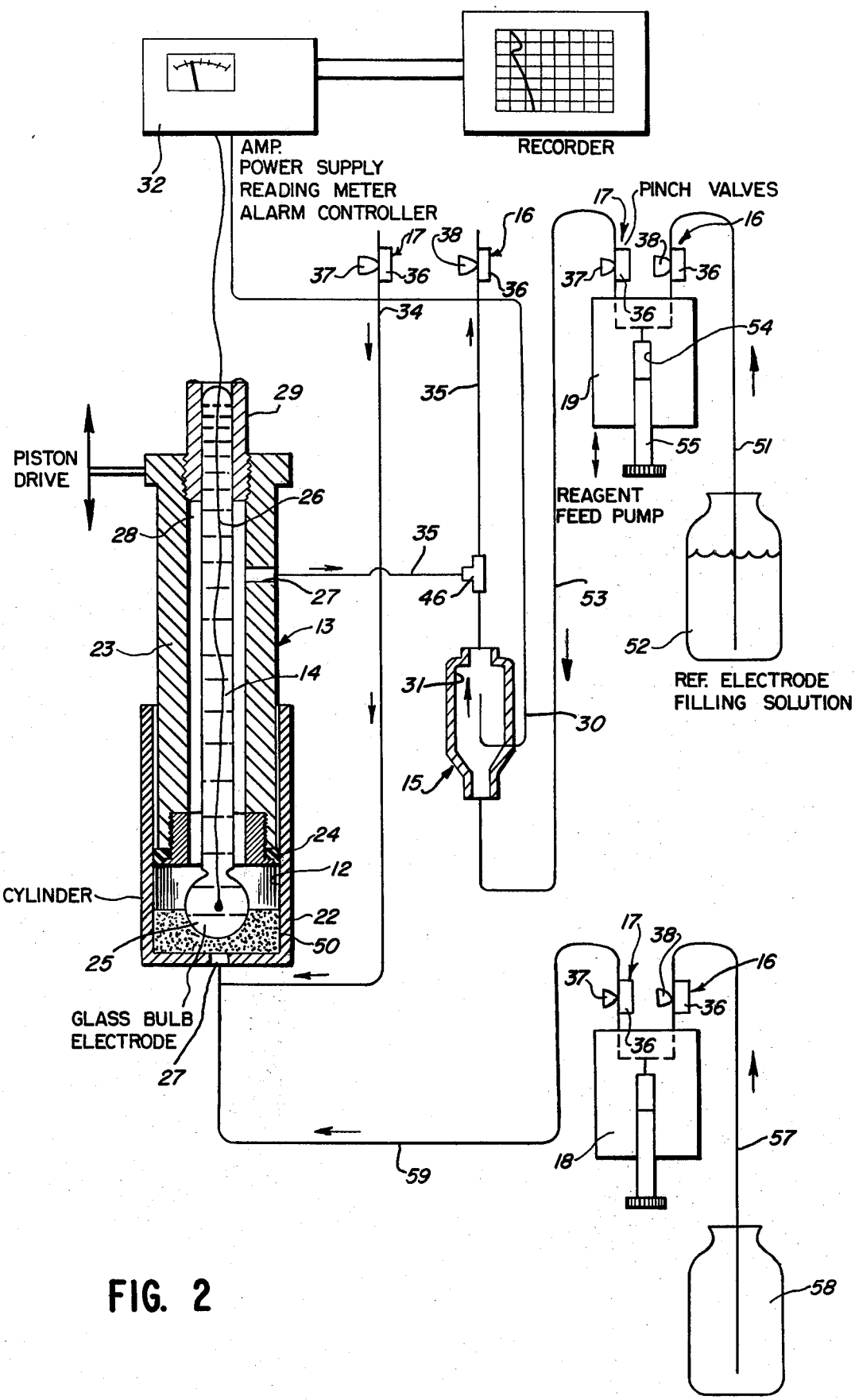

Other objects and advantages of the invention will become apparent upon reading the following detailed description and upon reference to the drawings, in which:

FIG. 1 is a partially schematic front elevation of a meter embodying the present invention; and FIG. 2 is a partially sectioned schematic of the meter shown in FIG. 1.

While the invention will be described in connection with a preferred embodiment, it will be understood that I do not intend to limit the invention to that embodiment. On the contrary, I intend to cover all alternatives, modifications and equivalents as may be included within the spirit and scope of the invention as defined by the appended claims.

Turning to the drawings, there is shown a meter 10 embodying the invention and including a plate-like frame 11 supporting a sample chamber 12, a piston 13 including a glass electrode 14 with the piston 13 being fitted for movement in the chamber 12, a reference electrode assembly 15, multiple line valve assemblies 16 and 17, positive displacement pumps 18 and 19, and a drive element 20 for controlling the piston 13, valve assemblies 16, 17 and positive displacement pumps 18, 19. With the exception of the piston 13 and the assembly 15, the overall arrangement and individual components are much like that disclosed in U.S. Pat. No. 3,953,136, issued Apr. 27, 1976.

The chamber 12 is preferably formed by a glass cylinder 22 and the piston 13 includes a body 23 mounting the electrode 14 and carrying a seal 24 tightly engaging the wall of the chamber 12. The measuring electrode 14 illustrated includes a glass body with a bulb head 25 in the chamber 12 with the entire electrode being filled with an ion solution such as silver chloride or calomel solution. A silver wire 26 is mounted in the electrode and serves as one element in the measuring circuit. The chamber 12 has inlet and outlet openings 27 connected by a narrow annular passage 28 surrounding the body of the electrode 14, which is held in place by being tightly fitted in a sleeve 29 threaded into the top of the body 23 and closing the passage 28.

The reference electrode assembly 15 includes a silver wire 30 mounted in an open-ended chamber 31 containing electrolytes such as potassium chloride that is in fluid communication with the outlet opening 27. The wires 26, 30 from the electrodes lead to the usual circuit 32 for detecting, amplifying and displaying the electrical potentials sensed, which can be scaled and presented as the pH of the sample solution. If desired, a recorder can make a running record of the meter's operation.

As described in said U.S. Pat. No. 3,953,136, samples are taken from a body of solution 33 being monitored through an intake line 34 that passes through the valve assembly 17, and samples are discharged from the chamber 12 through an outlet line 35 which passes through the valve assembly 16. Preferably, the lines 34, 35 are tough, flexible plastic tubing, and the valve assemblies 16, 17 are simply blocks 36 mounted on the frame against which the lines 34, 35 can be pinched shut by pinch levers 37 and 38, respectively, which are pivoted on the frame 11.

The drive element 20 is basically a cam journaled on the frame 11 and driven, counterclockwise in FIG. 1, by a synchronous motor or the like, not shown. A groove 41 in the element 20 carries a follower roller 42 mounted on a slide bar 43 that reciprocates in the frame 11 and is coupled directly to the piston 13. The periphery of the element 20 is also a cam lobe formed to operate the pinch levers 37, 38 which have rollers 44 riding on the element. As the element 20 rotates from the illustrated position, the intake line 34 is opened at the valve assembly 17, the outlet line 35 is pinched closed at the valve assembly 16, and the piston 13 rises to draw a liquid sample from the solution supply 33. During the next 180 degree rotation, the valve assemblies 16, 17 are reversed and the piston 13 moves down as illustrated to discharge the solution sample from the chamber 12 through the line 35.

In carrying out the invention, the glass measuring electrode is kept clean by having its bulb 25 plunged into a body of deformable material 50 during each stroke of the piston 13. Preferably, the body 50 is a bed of finely ground plastic grit that is inert to water pH variations, nonabrasive to glass, and having a specific gravity of more than one so that the grit will not float. An acrylic resin such as methyl methacrylate ground to about 30 mesh size particles has been found effective to mechanically scour and keep the bulb 25 clean as the piston 13 carries the bulb into the grit body 50 at each downstroke. To prevent fine grit particles from becoming wedged up in the passage 28, it is desirable to keep the passge 28 of small cross section and a spacing of only 1/64th of an inch has been found to be sufficient.

Pursuant to the invention, free and open electrical communication between the reference electrode wire 30 and the fluid in the chamber 12 is maintained by flowing electrolyte through the chamber 31, past the wire 30 and into the outlet line 35 through a fluid T-connector 46. To maintain this flow, the positive displacement pump 19 is connected by a line 51 passing through the valve assembly 16 to a supply of electrolyte 52, and is connected by a line 53 passing through the valve assembly 17 to the T-connector 46 and having chamber 31 of the reference electrode assembly 15 as a part of the line 53. The pump 19, as also shown in the aforementioned U.S. Pat. No. 3,953,136, includes a block containing a cylinder 54 in which a piston 55 is reciprocated through an arm 56 attached to the slide bar 43. From the position shown in FIG. 1, continued rotation of the drive element 20 will cause the valve assembly 16 to close the line 51 while the valve assembly 17 opens the line 53, and the slide bar 43 will be moved upwardly to insert the piston 55 into the chamber 54, thus forcing the measured amount of electrolyte in the chamber 54 into the reference electrode chamber 31. Continuing rotation of the drive element 20 will reverse the positions of the valve assemblies 16, 17 and downward movement of the slide 53 will cause the piston 55 to draw a measured amount of electrolyte through the line 51 and into the chamber 54.

The electrolyte flowing past the wire 30 moves through the T-connector 46 and into the line 35 toward the outlet opening 27, since the valve assembly 16 is then closing the line 35. On the next downstroke of the piston 13, the sample from the chamber 12 is driven through the line 35 to sweep the electrolyte through the upper portion of the T-connector 46. The sample cannot flow into the line 53 since the valve assembly 17 has then closed the line 53. There is no other flow of electrolyte from the line 53 into the line 35 since the specific gravity of the electrolyte is greater than water and the line 53 is coupled to the lower side of the T-connector 46. The positive displacement pump 19 is connected by a line 51 passing through the valve assembly 16 to a supply of electrolyte 52, and is connected by a line 53 passing through the valve assembly 17 to the T-connector 46 and having chamber 31 of the reference electrode assembly 15 as a part of the line 53. The pump 19, as also shown in the aforementioned U.S. Pat. No. 3,953,136, includes a block containing a cylinder 54 in which a piston 55 is reciprocated through an arm 56 attached to the slide bar 43. From the position shown in FIG. 1, continued rotation of the drive element 20 will cause the valve assembly 16 to close the line 51 while the valve assembly 17 opens the line 53, and the slide bar 43 will be moved upwardly to insert the piston 55 into the chamber 54, thus forcing the measured amount of electrolyte in the chamber 54 into the reference electrode chamber 31. Continuing rotation of the drive element 20 will reverse the position of the valve assemblies 16, 17 and downward movement of the slide 43 will cause the piston 55 to draw a measured amount of electrolyte through the line 51 and into the chamber 54.

As a feature of the invention, the second positive displacement pump 18 is connected by a line 57 passing through the valve assembly 16 to a supply 58 of a bacteria sterilizer such as formaldehyde, and is also connected by a line 59 passing through the valve assembly 17 and opening to the bottom of the chamber 12. The operation of the pump 18 is identical to that of the pump 19 so that, upon movement of the drive element 20 to the position illustrated in FIG. 1, a premeasured amount of bacteria sterilizer is drawn into the pump 18 and then, during the next one-half revolution of the element 20, that reagent is forced into the chamber 12. Utilization of this material is an option preventing the growth of bacterial slime within the meter during the testing of solutions containing live bacteria—such as sewage or river water.

It has also been found desirable to add to the supply 58 a wetting or surface active agent. Such a weak surfactant solution prevents air bubbles from adhering to the particles of grit making up the body of material 50. This prevents those particles from being floated up by tiny adhering air bubbles, and thus this maintains the desired bed of grit.

Those familiar with this art will appreciate that the meter 10 is a simple, relatively inexpensive assembly which, because of the continuous cleaning of the glass measuring electrode and the continuous maintenance of an unclogged, uncontaminated reference electrode connection provides accurate pH measurement for long-term, continuous monitoring. There is no mechanical junction between the reference electrode solution and the sample under test that could become fouled. The optional use of a sterilizer such as formaldehyde prevents bacteria growth from interfering with long-term operation of the pH meter.

I claim as my invention:

1. A pH meter comprising, in combination, a frame, a sample chamber mounted on said frame, a reference electrode mounted in fluid communication with said chamber, a piston mounted in said chamber and including a glass electrode to cooperate with said reference electrode for measuring the pH of liquid samples in the chamber, intake and outlet lines opening to said chamber, valves on said frame for each of said lines, means for reciprocating said piston in said chamber and operating said valves so that the outlet line is open and the intake line closed as the piston fills the chamber to exhaust fluid from the chamber and the intake line is open and the outlet line closed as the piston withdraws from the chamber and draws a new liquid sample into the chamber, said reference electrode mounting including an electrolyte line opening into said outlet line, a positive displacement pump in said frame driven by said means, said pump being connected to deliver controlled amounts of electrolyte past said reference electrode so as to maintain a flow of electrolyte into said outlet line, and a body of deformable material in said chamber and positioned to engage and clean said glass electrode each time said piston is reciprocated.

2. The combination of claim 1 in which said reference electrode mounting is a chamber forming part of said electrolyte line, and said electrolyte line opens into said outlet line through a T-connector with the electrolyte line being beneath the connector.

3. The combination of claim 1 including a second positive displacement pump on said frame driven by said means, said second pump being connected to deliver controlled amounts of a bacterial sterilizing agent to said chamber when liquid is being drawn into the chamber.

4. The combination of claim 1 in which said body is a bed of inert, nonabrasive, plastic grit.

5. The combination of claim 4 in which said grit is finely ground methyl methacrylate.

6. The combination of claim 4 including a second positive displacement pump on said frame driven by said means, said second pump being connected to deliver controlled amounts of a wetting surfactant to said chamber when liquid is being drawn into the chamber.

* * * * *